United States Patent
Hashimoto et al.

(10) Patent No.: US 10,391,052 B2
(45) Date of Patent: Aug. 27, 2019

(54) INJECTION PREPARATION AND METHOD FOR PRODUCING THE SAME

(71) Applicant: FUJIFILM CORPORATION, Minato-ku, Tokyo (JP)

(72) Inventors: Shinichi Hashimoto, Kanagawa (JP); Shigetomo Tsujihata, Kanagawa (JP); Yasuyuki Izumi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 15/269,989

(22) Filed: Sep. 20, 2016

(65) Prior Publication Data

US 2017/0007538 A1 Jan. 12, 2017

Related U.S. Application Data

(63) Continuation of application No. PCT/JP2014/084543, filed on Dec. 26, 2014.

(30) Foreign Application Priority Data

Mar. 28, 2014 (JP) ................. 2014-069613

(51) Int. Cl.
| | |
|---|---|
| A61K 31/519 | (2006.01) |
| A61K 9/00 | (2006.01) |
| A61K 47/20 | (2006.01) |
| A61K 9/08 | (2006.01) |
| A61K 47/18 | (2017.01) |

(52) U.S. Cl.
CPC .............. *A61K 9/0019* (2013.01); *A61K 9/08* (2013.01); *A61K 31/519* (2013.01); *A61K 47/183* (2013.01); *A61K 47/20* (2013.01)

(58) Field of Classification Search
CPC ......... A61K 31/519; A61K 9/08; A61K 47/06
USPC ....................................... 514/265.1; 424/400
See application file for complete search history.

(56) References Cited

U.S. PATENT DOCUMENTS

| | | | | |
|---|---|---|---|---|
| 6,686,365 | B2 * | 2/2004 | Riebesehl | A61K 45/06 |
| | | | | 514/262.1 |
| 9,884,061 | B2 * | 2/2018 | Hashimoto | A61K 9/08 |
| 2003/0212083 | A1 | 11/2003 | Riebesehl et al. | |
| 2015/0111905 | A1 * | 4/2015 | Khattar | A61K 9/0019 |
| | | | | 514/265.1 |
| 2015/0297724 | A1 * | 10/2015 | Park | A61K 31/198 |
| | | | | 514/265.1 |

FOREIGN PATENT DOCUMENTS

| | | |
|---|---|---|
| CN | 1396828 A | 2/2003 |
| JP | 2003-521518 A | 7/2003 |
| JP | 2013-540104 A | 10/2013 |
| WO | 01/56575 A1 | 8/2001 |
| WO | 2012/121523 A2 | 9/2012 |
| WO | 2013/179248 A1 | 12/2013 |

OTHER PUBLICATIONS

NIST, Monothioglycerol, http://webbook.nist.gov/cgi/cbook.cgi?ID=C96275&Units=CAL.*
NIST, Monothioglycerol, http://webbook.nist.gov/cgi?ID=C96275&Units=CAL (Year: 2016).*
International Search Report issued in International Application No. PCT/JP2014/084543 dated Apr. 7, 2015.
Written Opinion of the ISA issued in International Application No. PCT/JP2014/084543 dated Apr. 7, 2015.
Japanese Office Action dated Nov. 22, 2016 in corresponding Japanese Patent Application No. 2016-509917 and a Partial English Translation thereof.
Extended European Search Report dated Feb. 16, 2017, issued in corresponding EP Patent Application.
English language translation of the following: Office action dated Apr. 10, 2018 from the SIPO in a Chinese patent application No. 201480077586.X corresponding to the instant patent application. This office action translation is submitted now in order to supplement the understanding of the cited reference which is being disclosed in the instant information Disclosure Statement.

* cited by examiner

*Primary Examiner* — Shengjun Wang
(74) *Attorney, Agent, or Firm* — Solaris Intellectual Property Group, PLLC

(57) ABSTRACT

Provided are an injection preparation which includes: an aqueous composition containing pemetrexed or a salt thereof, at least one antioxidant agent A which is selected from the group consisting of cysteine and a salt thereof, and of which the content is 0.001 mass % to 0.1 mass % with respect to the total mass of the aqueous composition, thioglycerol of which the content is 0.001 mass % to 0.1 mass % with respect to the total mass of the aqueous composition, and an aqueous solvent of which the content is greater than or equal to 50 mass % with respect to the total mass of the aqueous composition, and a container which seals the aqueous composition, in which the concentration of oxygen in gas within the container which seals the aqueous composition is less than or equal to 2.0 volume %, and a method for producing the injection preparation.

11 Claims, No Drawings

INJECTION PREPARATION AND METHOD FOR PRODUCING THE SAME

CROSS-REFERENCE TO RELATED APPLICATIONS

This application is a continuation application of International Application No. PCT/JP2014/084543, filed Dec. 26, 2014, which is incorporated herein by reference. Further, this application claims priority from Japanese Patent Application No. 2014-069613, filed Mar. 28, 2014, which is incorporated herein by reference.

BACKGROUND OF THE INVENTION

1. Field of the Invention

The present invention relates to an injection preparation and a method for producing the same.

2. Description of the Related Art

Pemetrexed is a type of active ingredient of an anti-tumor therapeutic agent. An anticancer agent which contains pemetrexed as an active ingredient is administered to a patient through intravenous drip.

In JP2003-521518A, there is a disclosure of a liquid preparation obtained by using a combination of a specific antioxidant agent with pemetrexed.

In JP2013-540104A, there is a disclosure of a composition at a pH of 8 to 9.5 which is obtained by using a combination of at least one antioxidant agent which is selected from the group consisting of lipoic acid, dihydrolipoic acid, and methionine, at least one chelating agent which is selected from the group consisting of lactobionic acid and sodium citrate, and a pharmaceutically acceptable liquid, with pemetrexed.

In WO2012/121523A, there is a disclosure of a method for producing an injection agent by adjusting the concentration of dissolved oxygen in an injection solution which contains pemetrexed, but does not contain an antioxidant agent in an amount less than or equal to 1 ppm, and by adjusting the concentration of oxygen while filling an injection container with the injection solution in an amount less than or equal to 0.2 volume %.

SUMMARY OF THE INVENTION

An anticancer agent containing pemetrexed as an active ingredient is administered to a patient through intravenous drip. For this reason, the development of an injection preparation including an aqueous composition containing pemetrexed in which convenience and safety is considered when in use is desired.

However, in methods disclosed in JP2003-521518A, JP2013-540104A, and WO2012/121523A, preservation stability of an injection preparation during preservation, for example, the effect of suppressing decomposition of pemetrexed contained in an aqueous composition or a salt thereof, and coloration of an aqueous composition is not sufficiently exhibited.

The present invention has been made in consideration of the above-described circumstances, and an object of the present invention is to provide an injection preparation which can suppress coloration and decomposition of pemetrexed or a salt thereof during preservation, and a method for producing the same.

Specific means for solving the above-described problem is as follows.

<1> An injection preparation comprising:
an aqueous composition containing the following (i), (ii), (iii), and (iv); and
a container which seals the aqueous composition,
in which a concentration of oxygen in gas within the container which seals the aqueous composition is less than or equal to 2.0 volume %:
(i) pemetrexed or a salt thereof;
(ii) at least one antioxidant agent A which is selected from the group consisting of cysteine and a salt thereof, and of which the content is 0.001 mass % to 0.1 mass % with respect to the total mass of the aqueous composition;
(iii) thioglycerol of which the content is 0.001 mass % to 0.1 mass % with respect to the total mass of the aqueous composition; and
(iv) an aqueous solvent of which the content is greater than or equal to 50 mass % with respect to the total mass of the aqueous composition.

<2> An injection preparation comprising:
an aqueous composition containing the following (i), (ii), (iii), and (iv); and
a container which seals the aqueous composition,
in which a ratio (number of oxygen molecules/number of pemetrexed molecules) of the number of oxygen molecules with respect to the number of pemetrexed molecules in the injection preparation is less than or equal to 0.0160:
(i) pemetrexed or a salt thereof;
(ii) at least one antioxidant agent A which is selected from the group consisting of cysteine and a salt thereof, and of which the content is 0.001 mass % to 0.1 mass % with respect to the total mass of the aqueous composition;
(iii) thioglycerol of which the content is 0.001 mass % to 0.1 mass % with respect to the total mass of the aqueous composition; and
(iv) an aqueous solvent of which the content is greater than or equal to 50 mass % with respect to the total mass of the aqueous composition.

<3> The injection preparation according to <1> or <2>, in which a ratio of the content of the antioxidant agent A to the content of pemetrexed or a salt thereof in the aqueous composition (the content of pemetrexed or a salt thereof: the content of the antioxidant agent A) is 1:0.005 to 1:0.020 on a mass basis.

<4> The injection preparation according to <1> or <2>, in which a ratio of the content of thioglycerol to the content of pemetrexed or a salt thereof in the aqueous composition (the content of pemetrexed or a salt thereof: the content of thioglycerol) is 1:0.007 to 1:0.031 on a mass basis.

<5> The injection preparation according to <1> or <2>, in which a ratio of the content of thioglycerol to the content of the antioxidant agent A in the aqueous composition (the content of the antioxidant agent A: the content of thioglycerol) is 1:0.3 to 1:6.5 on a mass basis.

<6> The injection preparation according to <1> or <2>, in which at least one of a ratio of the content of the antioxidant agent A with respect to the content of pemetrexed or a salt thereof in the aqueous composition (the content of the antioxidant agent A/the content of pemetrexed or a salt thereof) being greater than or equal to 0.011 on a mass basis, or a ratio of the content of thioglycerol with respect to the content of pemetrexed or a salt thereof in the aqueous composition (the content of thioglycerol/the content of pemetrexed or a salt thereof) being greater than or equal to 0.015 on a mass basis is satisfied.

<7> The injection preparation according to any one of <1> to <6>, in which the pH of the aqueous composition is 7.0 to 9.0.

<8> A method for producing an injection preparation comprising:

preparing an aqueous composition which contains (i) pemetrexed or a salt thereof, (ii) at least one antioxidant agent A which is selected from the group consisting of cysteine and a salt thereof, and of which the content is 0.001 mass % to 0.1 mass % with respect to the total mass of the aqueous composition, (iii) thioglycerol of which the content is 0.001 mass % to 0.1 mass % with respect to the total mass of the aqueous composition, and (iv) an aqueous solvent of which the content is greater than or equal to 50 mass % with respect to the total mass of the aqueous composition; and filling a container with the aqueous composition under an inert gas atmosphere or substituting gas within the container with inert gas after filling the container with the aqueous composition.

<9> The method for producing an injection preparation according to <8>, in which the inert gas is nitrogen.

In the present specification, the numerical range represented by "to" means a range including numerical values denoted before and after "to" as a minimum value and a maximum value.

In the present specification, in a case where there are a plurality of substances corresponding to the respective components in a composition, the amount of each of the components in the composition means a total amount of the plurality of substances existing in the composition unless otherwise specified.

In the present specification, the term "step" is not only an independent step, and a case where a step cannot be clearly distinguished from other steps is also included in this term as long as an expected purpose of the step can be achieved.

According to the present invention, it is possible to provide the injection preparation which can suppress the coloration and the decomposition of pemetrexed or a salt thereof during preservation, and a method for producing the same.

DESCRIPTION OF THE PREFERRED EMBODIMENTS

Hereinafter, an injection preparation of the present invention will be described in details.

[Injection Preparation]

An injection preparation (hereinafter, referred to as a "first injection preparation") according to a first aspect of the present invention includes an aqueous composition which contains (i) pemetrexed or a salt thereof, (ii) at least one antioxidant agent A which is selected from the group consisting of cysteine and a salt thereof, and of which the content is 0.001 mass % to 0.1 mass % with respect to the total mass of the aqueous composition, (iii) thioglycerol of which the content is 0.001 mass % to 0.1 mass % with respect to the total mass of the aqueous composition, and (iv) an aqueous solvent of which the content is greater than or equal to 50 mass % with respect to the total mass of the aqueous composition; and a container which seals the aqueous composition, in which the concentration of oxygen in gas within the container which seals the aqueous composition is less than or equal to 2.0 volume %.

In addition, an injection preparation (hereinafter, referred to as a "second injection preparation") according to a second aspect of the present invention is an injection preparation including an aqueous composition; and a container which seals the aqueous composition, in which the aqueous composition contains (i) pemetrexed or a salt thereof, (ii) at least one antioxidant agent A which is selected from the group consisting of cysteine and a salt thereof, and of which the content is 0.001 mass % to 0.1 mass % with respect to the total mass of the aqueous composition, (iii) thioglycerol of which the content is 0.001 mass % to 0.1 mass % with respect to the total mass of the aqueous composition, and (iv) an aqueous solvent of which the content is greater than or equal to 50 mass % with respect to the total mass of the aqueous composition, and the ratio (number of oxygen molecules/number of pemetrexed molecules) of the number of oxygen molecules with respect to the number of pemetrexed molecules in the injection preparation is less than or equal to 0.0160.

It has been known that pemetrexed or a salt thereof is oxidatively decomposed in the injection preparation.

The injection preparation of the present invention can suppress the decomposition of pemetrexed or a salt thereof and the coloration of the aqueous composition during preservation, by sealing a combination of pemetrexed or a salt thereof, at least one antioxidant agent A which is selected from the group consisting of cysteine and a salt thereof, and of which the content is 0.001 mass % to 0.1 mass % with respect to the total mass of the aqueous composition, and thioglycerol of which the content is 0.001 mass % to 0.1 mass % with respect to the total mass of the aqueous composition, in a container, making the concentration of oxygen in gas within the container sealing the aqueous composition be less than or equal to 2.0 volume % in the first injection preparation, and making the ratio (number of oxygen molecules/number of pemetrexed molecules) of the number of oxygen molecules with respect to the number of pemetrexed molecules in the injection preparation be less than or equal to 0.0160 in the second injection preparation.

The present invention has been made by the present inventors who have found that it is possible to exhibit unexpected effects in which decomposition of pemetrexed or a salt thereof and generation of specific decomposition products are especially remarkably suppressed and coloration of an aqueous composition is also suppressed, by using a combination of pemetrexed or a salt thereof with at least one selected from the group consisting of thioglycerol and cysteine, and salts thereof.

The present inventors have also found that, if at least one selected from the group consisting of thioglycerol or cysteine and a salt thereof and sodium thioglycolate, which is similarly a type of antioxidant agent, are used together, the decomposition of pemetrexed or a salt thereof during preservation is not suppressed and specific decomposition products are remarkably generated.

[First Injection Preparation]

The first injection preparation is an injection preparation including an aqueous composition which contains (i) pemetrexed or a salt thereof, (ii) at least one antioxidant agent A which is selected from the group consisting of cysteine and a salt thereof, and of which the content is 0.001 mass % to 0.1 mass % with respect to the total mass of the aqueous composition, (iii) thioglycerol of which the content is 0.001 mass % to 0.1 mass % with respect to the total mass of the aqueous composition, and (iv) an aqueous solvent of which the content is greater than or equal to 50 mass % with respect to the total mass of the aqueous composition; and a container which seals the aqueous composition, in which the concentration of oxygen in gas within the container which seals the aqueous composition is less than or equal to 2.0 volume %.

Hereinafter, the aqueous composition, the container which seals the aqueous composition, the concentration of oxygen in gas within the container which seals the aqueous composition, and the like which are included in the first injection preparation of the present invention will be described.

<Aqueous Composition>

The aqueous composition contains (i) pemetrexed or a salt thereof, (ii) at least one antioxidant agent A which is selected from the group consisting of cysteine and a salt thereof, and of which the content is 0.001 mass % to 0.1 mass % with respect to the total mass of the aqueous composition, (iii) thioglycerol of which the content is 0.001 mass % to 0.1 mass % with respect to the total mass of the aqueous composition, and (iv) an aqueous solvent of which the content is greater than or equal to 50 mass % with respect to the total mass of the aqueous composition.

In addition, the aqueous composition may contain components other than (i), (ii), (iii), and (iv) as necessary.

(Pemetrexed or Salt Thereof)

The aqueous composition contains pemetrexed or a salt thereof.

Pemetrexed is an active ingredient of ALIMTA (registered trademark) which is produced and sold as an antimetabolite anti-malignant tumor agent by Eli Lilly Japan K.K.

As the salt of pemetrexed, any pharmaceutically acceptable salt may be used. Examples thereof include a salt of pemetrexed and alkali metal (for example, sodium or potassium), a salt of pemetrexed and alkali earth metal (for example, calcium or magnesium), a salt of pemetrexed and transition metal (for example, zinc, iron, cobalt, or copper), a salt of pemetrexed and basic ammonium, a salt of pemetrexed and triethanolamine, and a salt of pemetrexed and amino acid (for example, L-histidine, L-arginine, or L-lysine).

Pemetrexed or a salt thereof can be usually used singly, but two or more kinds thereof can also be used in combination.

As the salt of pemetrexed, at least one selected from the group consisting of pemetrexed sodium and pemetrexed potassium is preferable.

In pemetrexed or a salt thereof, a hydrate thereof is also included.

The concentration of pemetrexed or a salt thereof contained in an aqueous composition is preferably 0.1 mass % to 10.0 mass %, more preferably 0.5 mass % to 5.0 mass %, and still more preferably 1.0 mass % to 3.75 mass %, from the viewpoint of solubility and medicinal effect of pemetrexed.

In the present specification, in a case where two or more types of pemetrexed or a salt thereof are used in combination, the "concentration of pemetrexed or a salt thereof" means the total concentration of pemetrexed or a salt thereof used in combination.

(Antioxidant Agent A)

The aqueous composition contains at least one antioxidant agent A which is selected from the group consisting of cysteine and a salt thereof, and of which the content is 0.001 mass % to 0.1 mass % with respect to the total mass of the aqueous composition.

In the present invention, it is assumed that the antioxidant agent A contributes to suppression of the decomposition of pemetrexed or a salt thereof and to suppression of the coloration of the aqueous composition during preservation of the injection preparation, along with thioglycerol to be described below.

As the salt of cysteine, any pharmaceutically acceptable salt may be used. Examples thereof include a salt of cysteine and alkali metal (for example, sodium or potassium), a salt of cysteine and alkali earth metal (for example, calcium or magnesium), a salt of cysteine and transition metal (for example, zinc, iron, cobalt, or copper), a salt of cysteine and basic ammonium, a salt of cysteine and triethanolamine, a salt of cysteine and amino acid (for example, L-histidine, L-arginine, or L-lysine), and a salt of cysteine and hydrochloric acid, sulfuric acid, phosphoric acid, formic acid, acetic acid, maleic acid, fumaric acid, or tartaric acid.

As the salt of cysteine, at least one selected from the group consisting of cysteine hydrochloride, cysteine sulfate, cysteine phosphate, cysteine formate, and cysteine acetate is preferable and cysteine hydrochloride is more preferable from the viewpoint of extremely low toxicity to human bodies.

The aqueous composition may contain one type of antioxidant agent A, or may contain two or more types thereof.

The content of the antioxidant agent A contained in the aqueous composition is 0.001 mass % to 0.1 mass % with respect to the total mass of the aqueous composition.

If the content of the antioxidant agent A contained in the aqueous composition is smaller than 0.001 mass % with respect to the total mass of the aqueous composition, it is difficult to suppress the decomposition of pemetrexed or a salt thereof and the coloration of the aqueous composition during preservation. In addition, if the content of the antioxidant agent A contained in the aqueous composition is larger than 0.1 mass % with respect to the total mass of the aqueous composition, it is difficult to apply the injection preparation to human bodies.

The content of the antioxidant agent A contained in the aqueous composition is preferably 0.010 mass % to 0.051 mass %, more preferably 0.020 mass % to 0.051 mass %, and still more preferably 0.024 mass % to 0.051 mass % with respect to the total mass of the aqueous composition from the viewpoint of being capable of remarkably suppressing the decomposition of pemetrexed or a salt thereof and the coloration of the aqueous composition during preservation.

The ratio of the content of the antioxidant agent A to the content of pemetrexed or a salt thereof in the aqueous composition (the content of pemetrexed or a salt thereof: the content of the antioxidant agent A) is preferably 1:0.0004 to 1:0.020, more preferably 1:0.005 to 1:0.020, and still more preferably 1:0.011 to 1:0.020 on a mass basis.

The "content of pemetrexed or a salt thereof" in the present invention means a pemetrexed conversion value.

If the ratio of the content of the antioxidant agent A to the content of pemetrexed or a salt thereof in the aqueous composition (the content of pemetrexed or a salt thereof: the content of the antioxidant agent A) is within the above-described range, the decomposition of pemetrexed or a salt thereof and the coloration of the aqueous composition during preservation can be remarkably suppressed.

(Thioglycerol)

The aqueous composition contains thioglycerol of which the content is 0.001 mass % to 0.1 mass % with respect to the total mass of the aqueous composition.

In the present invention, thioglycerol contributes to suppression of the decomposition of pemetrexed or a salt thereof and to suppression of the coloration of the aqueous composition during preservation of the injection preparation, along with the above-described antioxidant agent A.

The content of thioglycerol contained in the aqueous composition is 0.001 mass % to 0.1 mass % with respect to the total mass of the aqueous composition.

If the content of thioglycerol contained in the aqueous composition is smaller than 0.001 mass % with respect to the total mass of the aqueous composition, it is difficult to suppress the decomposition of pemetrexed or a salt thereof and the coloration of the aqueous composition during preservation. In addition, if the content of thioglycerol contained in the aqueous composition is larger than 0.1 mass % with respect to the total mass of the aqueous composition, it is difficult to apply the injection preparation to human bodies.

The content of thioglycerol contained in the aqueous composition is preferably 0.010 mass % to 0.076 mass %, more preferably 0.020 mass % to 0.076 mass %, and still more preferably 0.036 mass % to 0.076 mass % with respect to the total mass of the aqueous composition from the viewpoint of being capable of remarkably suppressing the decomposition of pemetrexed or a salt thereof and the coloration of the aqueous composition during preservation.

The ratio of the content of thioglycerol to the content of pemetrexed or a salt thereof in the aqueous composition (the content of pemetrexed or a salt thereof: the content of thioglycerol) is preferably 1:0.0012 to 1:0.031, more preferably 1:0.007 to 1:0.031, and still more preferably 1:0.015 to 1:0.031 on a mass basis.

As described above, the "content of pemetrexed or a salt thereof" in the present invention means a pemetrexed conversion value.

If the ratio of the content of thioglycerol to the content of pemetrexed or a salt thereof in the aqueous composition (the content of pemetrexed or a salt thereof: the content of thioglycerol) is within the above-described range, it is possible to remarkably suppress the decomposition of pemetrexed or a salt thereof and the coloration of the aqueous composition during preservation.

The ratio of the content of thioglycerol to the content of the antioxidant agent A in the aqueous composition (the content of the antioxidant agent A: the content of thioglycerol) is preferably 1:0.3 to 1:6.5, more preferably 1:0.5 to 1:3.2, and still more preferably 1:0.7 to 1:2.1 on a mass basis.

If the ratio of the content of thioglycerol to the content of the antioxidant agent A in the aqueous composition (the content of the antioxidant agent A: the content of thioglycerol) is within the above-described range, it is possible to remarkably suppress the decomposition of pemetrexed or a salt thereof and the coloration of the aqueous composition during preservation.

In the injection preparation of the present invention, it is preferable that any one of the ratio of the content of the antioxidant agent A with respect to the content of pemetrexed or a salt thereof in the aqueous composition (the content of the antioxidant agent A/the content of pemetrexed or a salt thereof) being greater than or equal to 0.011 on a mass basis and the ratio of the content of thioglycerol with respect to the content of pemetrexed or a salt thereof in the aqueous composition (the content of thioglycerol/the content of pemetrexed or a salt thereof) being greater than or equal to 0.015 on a mass basis is satisfied, and it is more preferable that both of the ratio of the content of the antioxidant agent A with respect to the content of pemetrexed or a salt thereof in the aqueous composition (the content of the antioxidant agent A/the content of pemetrexed or a salt thereof) being greater than or equal to 0.011 on a mass basis and the ratio of the content of thioglycerol with respect to the content of pemetrexed or a salt thereof in the aqueous composition (the content of thioglycerol/the content of pemetrexed or a salt thereof) being greater than or equal to 0.015 on a mass basis is satisfied from the viewpoint of being capable of remarkably suppressing the coloration of the aqueous composition during preservation of the injection preparation.

(Aqueous Solvent)

The aqueous composition contains an aqueous solvent of which the content is greater than or equal to 50 mass % with respect to the total mass of the aqueous composition.

The aqueous solvent is not particularly limited as long as the aqueous solvent can be used in the injection preparation, and examples thereof include water and a solvent which is mixed with a medium that can be mixed with water.

Specific examples of the aqueous solvent include injection water (distilled water for injection), a normal saline solution, distilled water, a glucose solution, and ultrapure water.

The aqueous solvent may contain an arbitrary component, which functions as a pH adjusting agent or the like, such as organic acid, an organic base, inorganic acid, an inorganic base, or salts thereof.

In addition, the aqueous solvent may be a buffer solution which has a buffering capacity.

The content of the aqueous solvent contained in the aqueous composition with respect to the total mass of the aqueous composition is preferably greater than or equal to 60 mass %, more preferably greater than or equal to 70 mass %, still more preferably greater than or equal to 80 mass %, and particularly preferably greater than or equal to 90 mass %.

(pH Adjusting Agent)

It is preferable that the aqueous composition further contains a pH adjusting agent.

The pH adjusting agent is not particularly limited as long as the pH adjusting agent is pharmaceutically acceptable.

Specifically, it is preferable that the pH adjusting agent is at least one selected from the group consisting of hydrochloric acid, sodium hydroxide, potassium hydroxide, magnesium hydroxide, calcium hydroxide, phosphoric acid or a salt thereof, citric acid or a salt thereof, tartaric acid or a salt thereof, acetic acid or a salt, succinic acid or a salt thereof, lactic acid or a salt thereof, gluconic acid or a salt thereof, adipic acid or a salt thereof, fumaric acid or a salt thereof, boric acid or a salt thereof, maleic acid or a salt thereof, methanesulfonic acid or a salt thereof, malic acid or a salt thereof, triethanolamine, monoethanolamine, diisopropanolamine, triisopropanolamine, trometamol (tris hydroxymethyl aminomethane), glycine, meglumine, and disodium edetate, and it is more preferable that the pH conditioner is at least one selected from the group consisting of hydrochloric acid, sodium hydroxide, phosphoric acid or a salt thereof, citric acid or a salt thereof, triethanolamine, trometamol (tris hydroxymethyl aminomethane), and disodium edetate.

In a case where the aqueous composition contains a pH adjusting agent, one kind of pH adjusting agent may be used or two or more kinds may be used.

The phosphate or the citrate may be a pharmaceutically acceptable salt, and examples thereof include a salt of phosphoric acid or citric acid and alkali metal (for example, sodium or potassium), a salt of phosphoric acid or citric acid and alkali earth metal (for example, calcium or magnesium), a salt of phosphoric acid or citric acid and transition metal (for example, zinc, iron, cobalt, or copper), a salt of phosphoric acid or citric acid and basic ammonium, a salt of phosphoric acid or citric acid and triethanolamine, and a salt of phosphoric acid or citric acid and amino acid (for example, L-histidine, L-arginine, or L-lysine).

As the phosphate, disodium hydrogen phosphate, sodium dihydrogen phosphate, potassium dihydrogen phosphate and the like are preferable, and as the citrate, trisodium citrate, disodium citrate, sodium dihydrogen citrate, and the like are preferable.

In a case where the aqueous composition contains a pH adjusting agent, the pH adjusting agent is more preferably at least one selected from the group consisting of citric acid and citrate and still more preferably at least one selected from the group consisting of trisodium citrate and disodium citrate from the viewpoint of suppressing generation of insoluble impurities which can be generated during preservation.

The content of the pH adjusting agent in the aqueous composition is not particularly limited, and can be appropriately set in accordance with the type of pH adjusting agent or the like.

(Other Components)

The aqueous composition may contain other pharmaceutically acceptable components as necessary in addition to pemetrexed or a salt thereof, the antioxidant agent A, thioglycerol, the aqueous solvent, and the pH adjusting agent as an arbitrary component, within the scope not impairing the purpose of the present invention.

Examples of the other components include a tonicity agent, a stabilizing agent, a solubilizing agent, a surfactant, a long-lasting agent, an anti-foaming agent, a coloring agent, an emulsifying agent, a dispersing agent, a preservative, a preserving agent, a solubilizer, and a solvent. However, the other components are not limited to these components.

The content of the other components can be appropriately set within the scope of exhibiting the effect of the present invention.

(pH of Aqueous Composition)

The pH of the aqueous composition is preferably 5.5 to 9.5, more preferably 7.0 to 9.0, and still more preferably 7.8 to 9.0.

If the pH of the aqueous composition is within the above-described range, it is possible to remarkably suppress the decomposition of pemetrexed or a salt thereof during preservation.

In the present specification, the pH is measured by setting the temperature of the injection preparation to 25° C.

The method for measuring the pH is not particularly limited, and a usually used method can be used as the method for measuring the pH. The measurement of the pH can be performed using, for example, a pH meter (device number: F-73, manufactured by Horiba, Ltd., pH electrode: MICRO TOUPH electrode 9618-10D).

<Container>

The injection preparation of the present invention is an injection preparation in a container which includes a container which seals the above-described aqueous composition.

Examples of the container which seals the aqueous composition include a vial bottle, an ampule, and a syringe. Among these, a vial bottle is preferable as the container which seals the aqueous composition from the viewpoint of handling properties in a medical site.

In addition, a container in which the amount of silicon eluted into water in a case where the container is filled with water and heat treatment is performed for 60 minutes at 121° C. is less than or equal to 1.0 ppm is preferable as the container which seals the aqueous composition, and a container in which the amount of silicon eluted into water in a case where the container is filled with water and heat treatment is performed for 60 minutes at 121° C. is less than or equal to 0.5 ppm is more preferable as the container which seals the aqueous composition.

It is possible to use a commercially available product as the container which seals the aqueous composition, and it is possible to use, for example, Resin CZ manufactured by Daikyo Seiko. Ltd., 3010, 3010 SILICORT, FY-5, FY-5 SILICORT, FY-5 SULFUR TREATMENT, CS-20 SILICORT, CS-30 SILICORT, and CS-40 SILICORT which are manufactured by Fuji Glass Co., Ltd., 23×43 LA, 23×43 VIST which are manufactured by Daiwa Special Glass Co., Ltd., or the like as the commercially available product of the container which seals the aqueous composition.

It is possible to improve preservation stability of pemetrexed or a salt thereof contained in the aqueous composition using a film with oxygen barrier properties, as a package of the container which seals the aqueous composition.

As the material of the film, alumina-coated PET (polyethylene terephthalate), silica-coated PET, nanocomposite-coated PET, PET, polyvinyl alcohol, an ethylene-vinyl alcohol copolymer, polyvinyl chloride, polyvinylidene chloride, a vinylidene chloride-methyl acrylate copolymer, meta-xylylene adipamide 6 nylon, biaxially stretched nylon, non-stretched nylon, biaxially stretched polypropylene, high density polyethylene, non-stretched polypropylene, polycarbonate, polystyrene, low density polyethylene, or the like can be used.

The oxygen gas permeability of the film is preferably less than or equal to 100 $cm^3/m^2 \cdot 24$ h·atm, more preferably less than or equal to 10 $cm^3/m^2 \cdot 24$ h·atm, and still more preferably less than or equal to 2 $cm^3/m^2 \cdot 24$ h·atm, from the viewpoint of preservation stability.

The container which seals the aqueous composition may be single packaged using a film with oxygen barrier properties, or may be multiply packaged using a plurality of films with oxygen barrier properties.

In the injection preparation of the present invention, it is possible to fill any one space between the container and the outermost package which packages the container, with a deoxidizing agent from the viewpoint of improving preservation stability of pemetrexed or a salt thereof.

As the deoxidizing agent, it is possible to use an iron-based self-reactive deoxidizing agent (manufactured by Mitsubishi Gas Chemical Company, Inc., AGELESS ZP, AGELESS ZJ-PT, AGELESS ZJ-PK, AGELESS S, or the like), an iron-based moisture-dependent deoxidizing agent (manufactured by Mitsubishi Gas Chemical Company, Inc., Ageless FX, or the like), a nonferrous self-reactive deoxidizing agent (manufactured by Mitsubishi Gas Chemical Company, Inc., Ageless GLS, Ageless GL-M, Ageless GT, or the like), and the like.

<Concentration of Oxygen in Gas within Container>

In the first injection preparation of the present invention, the concentration of oxygen in gas within the container which seals the aqueous composition is less than or equal to 2.0 volume %.

In the first injection preparation of the present invention, if the concentration of oxygen in gas within the container which seals the aqueous composition exceeds 2.0 volume %, it is difficult to suppress the decomposition of pemetrexed or a salt thereof and coloration of the aqueous composition during preservation.

In the first injection preparation of the present invention, the concentration of oxygen in gas within the container which seals the aqueous composition is preferably less than or equal to 1.5 volume %, more preferably less than or equal to 1.0 volume %, still more preferably less than or equal to 0.5 volume %, and particularly preferably less than or equal to 0.2 volume % from the viewpoint of being capable of remarkably suppressing the decomposition of pemetrexed or a salt thereof and the coloration of the aqueous composition during preservation. It is most preferable that oxygen is not contained in gas within the container which seals the aqueous composition.

In the concentration of oxygen in gas within the container in the present invention, any of measurement of the concentration of oxygen in gas sealed in the container during the production of the injection preparation, measurement of the concentration of oxygen in gas within the container immediately after the production of the injection preparation, or measurement of the concentration of oxygen in gas within the container after preserving the injection preparation for a certain period is included.

Gas within the container which seals the aqueous composition is preferably substituted with inert gas. Nitrogen is preferable as inert gas. Using inert gas (in particular, nitrogen), it is possible to easily adjust the concentration of oxygen in gas within the container which seals the aqueous composition.

The method for measuring the concentration of oxygen in gas within the container is not particularly limited, and it is possible to use a method, which is generally used, as the method for measuring the concentration of oxygen in gas. For example, the concentration of oxygen in gas within the container can be measured using an oxygen monitor (product name: OXY-1, manufactured by Jikco Ltd., measurement method: diaphragm-type galvanic cell type) or a residual oxygen meter (product name: PACK MASTER, manufactured by Iijima Electronics Corporation, measurement method: diaphragm-type galvanic cell type).

Specific examples of the method for measuring the concentration of oxygen in gas within the container include a method for measuring the concentration of oxygen in gas by reading a display value on a sensor-incorporated oxygen monitor in a glove box when producing an injection preparation while controlling the amount of nitrogen and oxygen which have been injected, so as to have a target oxygen concentration in the glove box (minimum resolution: 0.1%) or a method for measuring the concentration of oxygen in gas by sticking a sampler needle portion of the oxygen concentration determination device into a container of an injection preparation and suctioning gas in a head space within the container (minimum resolution: 0.01%). In the case of the latter method, it is preferable to measure the concentration thereof under a nitrogen atmosphere (concentration of oxygen in gas: less than 0.1 v/v %) in order to avoid oxygen outside the container from being mixed in during the measurement.

<Concentration of Dissolved Oxygen in Aqueous Composition>

The concentration of dissolved oxygen in an aqueous composition is preferably less than or equal to 9 ppm, more preferably less than or equal to 7 ppm, still more preferably less than or equal to 3 ppm, particularly preferably less than or equal to 0.5 ppm, and particularly preferably less than or equal to 0.1 ppm.

If the concentration of dissolved oxygen in an aqueous composition is less than or equal to 9 ppm, it is possible to remarkably suppress the decomposition of pemetrexed or a salt thereof and the coloration of the aqueous composition during preservation.

The method for measuring the concentration of dissolved oxygen in an aqueous composition is not particularly limited, and it is possible to use a method, which is generally used, as the method for measuring the concentration of dissolved oxygen in a solution. For example, it is possible to measure the concentration of dissolved oxygen in an aqueous composition using an oxygen concentration determination device (product name: InLab (registered trademark) Science Pro ISM, manufactured by Mettler-Toledo International Inc.) or a residual oxygen meter (product name: Pack Master, manufactured by Iijima Electronics Corporation).

Specific examples of the method for measuring the concentration of dissolved oxygen in an aqueous composition include a method for measuring the concentration of dissolved oxygen in an aqueous composition by bringing an electrode of the oxygen concentration determination device into contact with the aqueous composition under nitrogen atmosphere (oxygen concentration: less than or equal to 0.1 volume %) in the glove box, or a method for measuring the concentration of dissolved oxygen in an aqueous composition by sticking a sampler needle portion of the oxygen concentration determination device into a container included in an injection preparation and suctioning the aqueous composition in the container.

In addition, in a case of measuring the concentration of dissolved oxygen in an aqueous composition which has been preserved for one or more days, it is considered that oxygen dissolved in the aqueous composition and oxygen existing in gas within the container reach equilibrium. Therefore, it is possible to calculate the concentration of oxygen in the aqueous composition by, for example, measuring the concentration of oxygen in gas within the container from Henry's law.

[Second Injection Preparation]

The second injection preparation of the present invention is an injection preparation including an aqueous composition; and a container which seals the aqueous composition, in which the aqueous composition contains (i) pemetrexed or a salt thereof, (ii) at least one antioxidant agent A which is selected from the group consisting of cysteine and a salt thereof, and of which the content is 0.001 mass % to 0.1 mass % with respect to the total mass of the aqueous composition, (iii) thioglycerol of which the content is 0.001 mass % to 0.1 mass % with respect to the total mass of the aqueous composition, and (iv) an aqueous solvent of which the content is greater than or equal to 50 mass % with respect to the total mass of the aqueous composition, and the ratio (number of oxygen molecules/number of pemetrexed molecules) of the number of oxygen molecules with respect to the number of pemetrexed molecules in the injection preparation is less than or equal to 0.0160.

Hereinafter, the second injection preparation of the present invention will be described. The description of the aqueous composition, the container, the concentration of dissolved oxygen in an aqueous composition, and the like will not be repeated since the matters described in the section of the above-described first injection preparation can be applied as they are, and only the different points will be described.

<Ratio of Number of Oxygen Molecules with Respect to Number of Pemetrexed Molecules in Injection Preparation>

In the second injection preparation of the present invention, the ratio (number of oxygen molecules/number of pemetrexed molecules) of the number of oxygen molecules with respect to the number of pemetrexed molecules in the injection preparation is less than or equal to 0.0160.

In the second injection preparation of the present invention, if the ratio (number of oxygen molecules/number of pemetrexed molecules) of the number of oxygen molecules with respect to the number of pemetrexed molecules in the injection preparation exceeds 0.0160, it is difficult to suppress the decomposition of pemetrexed or a salt thereof and the coloration of the aqueous composition during preservation.

In the second injection preparation of the present invention, the ratio (number of oxygen molecules/number of pemetrexed molecules) of the number of oxygen molecules with respect to the number of pemetrexed molecules in the injection preparation is preferably less than or equal to 0.0080, more preferably less than or equal to 0.0040, and still more preferably less than or equal to 0.0020 from the viewpoint of being capable of remarkably suppressing the decomposition of pemetrexed or a salt thereof and the coloration of the aqueous composition during preservation.

When an aqueous composition is sealed in a container, the ratio (number of oxygen molecules/number of pemetrexed molecules) of the number of oxygen molecules with respect to the number of pemetrexed molecules in the injection preparation is calculated based on the total number of oxygen molecules which has been calculated by multiplying the concentration of oxygen in gas within the container by the volume thereof and multiplying the concentration of dissolved oxygen in the aqueous composition by the volume thereof. In addition, when no aqueous composition is sealed in a container or when an aqueous composition is sealed in a container and there is no gas in the container (for example, prefilled syringe), the ratio (number of oxygen molecules/number of pemetrexed molecules) of the number of oxygen molecules with respect to the number of pemetrexed molecules in the injection preparation is calculated based on the concentration of dissolved oxygen in the aqueous composition.

In the ratio (number of oxygen molecules/number of pemetrexed molecules) of the number of oxygen molecules with respect to the number of pemetrexed molecules in the injection preparation in the present invention, any of a ratio measured and calculated during the production of the injection preparation, a ratio measured and calculated immediately after the production of the injection preparation, or a ratio measured and calculated after preserving the injection preparation for a certain period is included.

In the present specification, the number of pemetrexed molecules in the injection preparation and the number of oxygen molecules in the injection preparation are respectively calculated in accordance with the following methods.

Number (mol) of pemetrexed molecules in injection preparation=concentration (mol/L) of pemetrexed in aqueous composition×volume (L) of aqueous composition  Equation 1.

Number (mol) of oxygen molecules in injection preparation=number (mol) of oxygen molecules in gas within container+number (mol) of oxygen molecules in aqueous composition  Equation 2.

Number (mol) of oxygen molecules in gas within container=concentration (volume %) of oxygen in gas within container÷100×volume (L) of gas within container÷(0.082×(273.15+temperature (° C.)))  Equation 3.

Number (mol) of oxygen molecules in aqueous composition=concentration (mg/L) of dissolved oxygen in aqueous composition÷32÷1000×volume (L) of aqueous composition  Equation 4.

In a case where the method for measuring the concentration of oxygen in gas within the container is a method in which a display value of a sensor-incorporated oxygen monitor in a glove box is read when an injection preparation is prepared while controlling the amounts of nitrogen and oxygen, which have been injected, so as to have a target oxygen concentration in the glove box, the temperature in Equation 3 refers to temperature when the aqueous composition is sealed.

In contrast, in a case where the method for measuring the concentration of oxygen in gas within the container is a method in which the concentration of oxygen in gas is measured by sticking a sampler needle portion of an oxygen concentration determination device into the container of an injection preparation and suctioning gas in a head space within the container in the injection preparation, the temperature in Equation 3 refers to temperature during the measurement.

[Method for Producing Injection Preparation]

The method (hereinafter, referred to as a "production method") for producing an injection preparation of the present invention includes: preparing (hereinafter, also referred to as an "aqueous composition preparation step") an aqueous composition which contains (i) pemetrexed or a salt thereof, (ii) at least one antioxidant agent A which is selected from the group consisting of cysteine and a salt thereof, and of which the content is 0.001 mass % to 0.1 mass % with respect to the total mass of the aqueous composition, (iii) thioglycerol of which the content is 0.001 mass % to 0.1 mass % with respect to the total mass of the aqueous composition, and (iv) an aqueous solvent of which the content is greater than or equal to 50 mass % with respect to the total mass of the aqueous composition; and filling (hereinafter, also referred to as a "filling step") a container with the aqueous composition under an inert gas atmosphere or substituting (hereinafter, referred to as a "substituting step") gas within the container with inert gas after filling the container with the aqueous composition.

The production method of the present invention may include other steps as necessary.

The injection preparation which has been produced in this manner can exhibit an effect of suppressing decomposition of pemetrexed or a salt thereof and an effect of suppressing coloration of an aqueous composition during preservation.

Hereinafter, the production method of the present invention will be described. Description of matters, for example, the components contained in the aqueous composition, the amount thereof, and the container, which are in common with the above-described injection preparation of the present invention will not be repeated.

(Aqueous Composition Preparation Step)

The aqueous composition preparation step is a step of preparing an aqueous composition which contains (i) pemetrexed or a salt thereof, (ii) at least one antioxidant agent A which is selected from the group consisting of cysteine and a salt thereof, and of which the content is 0.001 mass % to 0.1 mass % with respect to the total mass of the aqueous composition, (iii) thioglycerol of which the content is 0.001 mass % to 0.1 mass % with respect to the total mass of the aqueous composition, and (iv) an aqueous solvent of which the content is greater than or equal to 50 mass % with respect to the total mass of the aqueous composition.

The method for preparing an aqueous composition is not particularly limited as long as it is possible to visually check that the aqueous composition after the preparation is a homogeneous and clear solution.

Examples of the method for preparing an aqueous composition include a method for gradually adding pemetrexed or a salt thereof, the antioxidant agent A, and thioglycerol to an aqueous solvent while stirring the aqueous solvent to dissolve these components in the aqueous solvent.

The temperature conditions when dissolving pemetrexed or a salt thereof in the aqueous solvent are not particularly limited, and can be appropriately set in accordance with the composition (types and content) of the components dissolved in the aqueous solvent. In general, it is possible to dissolve a pH adjusting agent and the above-described other components as necessary in addition to pemetrexed or a salt thereof, the antioxidant agent A, and thioglycerol therein after setting the conditions of the temperature of an aqueous medium to 0° C. to 35° C.

(Filling Step)

The filling step is a step of filling a container with an aqueous composition under an inert gas atmosphere.

In the filling step, the method for filling a container with an aqueous composition under an inert gas atmosphere is not particularly limited, and a well-known method can be employed.

Nitrogen is preferable as inert gas.

In the filling step, it is possible to obtain the first injection preparation of the present invention by filling a container with an aqueous composition under an inert gas atmosphere such that the concentration of oxygen in gas within the container which seals the aqueous composition becomes less than or equal to 2.0 volume %.

In addition, in the filling step, it is possible to obtain the second injection preparation of the present invention by filling a container with an aqueous composition under an inert gas atmosphere such that the ratio (number of oxygen molecules/number of pemetrexed molecules) of the number of oxygen molecules with respect to the number of pemetrexed molecules in the injection preparation becomes less than or equal to 0.0160.

(Substituting Step)

The substituting step is a step of substituting gas within a container with inert gas after the container is filled with an aqueous composition.

In the substituting step, the method for substituting gas within the container, which is filled with an aqueous composition, with inert gas is not particularly limited, and a well-known method can be employed.

Nitrogen is preferable as inert gas.

In the substituting step, it is possible to obtain the first injection preparation of the present invention by substituting gas within the container with inert gas after filling the container with an aqueous composition such that the concentration of oxygen in gas within the container which seals the aqueous composition becomes less than or equal to 2.0 volume %.

In addition, in the substituting step, it is possible to obtain the second injection preparation of the present invention by substituting gas within the container with inert gas after filling the container with an aqueous composition such that the ratio (number of oxygen molecules/number of pemetrexed molecules) of the number of oxygen molecules with respect to the number of pemetrexed molecules in the injection preparation becomes less than or equal to 0.0160.

The device used in the substituting step is not particularly limited. For example, it is possible to use a glove box, a capping machine or a vacuum capping machine which has a function of capping under an inert gas stream, or a chamber which has a function of capping in a sealed state.

Specific examples of the substituting method include a method for substituting gas within a container (vial) with inert gas by tightly plugging the vial in a glove box using a rubber plug after the vial, which is filled with an aqueous composition, and the rubber plug are placed in the glove box and inert gas is blown to the inside of the glove box so as to have a target oxygen concentration in the glove box. In addition, another example of the substituting method include a method for substituting gas within a container (vial) with inert gas by repeating evacuating and blowing of inert gas after blocking the vial filled with an aqueous composition from outside air by covering the vial with a chamber component. In addition, still another example of the substituting method include a method for substituting gas within a container (vial) with inert gas by tightly plugging the vial in a chamber which has a function of capping in a sealed state after installing the half-capped vial in the chamber and blowing inert gas into the chamber so as to have a target oxygen concentration.

(Other Steps)

The production method of the present invention may include steps other than the above-described aqueous composition preparation step, filling step, and substituting step as necessary.

Examples of the other steps include a pH adjusting step of adjusting the pH of the aqueous composition obtained in the aqueous composition preparation step.

The method for adjusting the pH of the aqueous composition is not particularly limited, and the pH can be adjusted using, for example, the above-described pH adjusting agent.

Regarding a usual method for producing an injection preparation, it is possible to refer to, for example, the disclosure of JP2003-521518A.

EXAMPLES

Hereinafter, the present invention will be more specifically described using Examples. However, the present invention is not limited to the following Examples as long as Examples do not depart from the gist of the present invention.

Example 1: Preparation of Injection Preparation (C-1)

2.00 g of injection water (manufactured by Hikari Pharmaceutical Co., Ltd.), pemetrexed disodium (62.5 mg as pemetrexed), 128.0 mg of a 1 mass % aqueous solution of cysteine hydrochloride (manufactured by KYOWA HAKKO BIO CO. LTD., L-cysteine hydrochloride monohydrate) which had been prepared in advance, and 190.0 mg of 1 mass % aqueous solution of thioglycerol (manufactured by ASAHI KAGAKU KOGYO Co., Ltd., 1-thioglycerol) which had been prepared in advance were weighed into a clean 10 mL vial in which a stirrer was placed, and were stirred and dissolved for 10 minutes at room temperature. Determination as to whether or not the mixed solution became a homogeneous and clear solution was performed through visual observation. Specifically, it was determined that the dissolution was completed when dissolution residues were not recognized while externally observing the mixed solution with the naked eye.

An aqueous composition was obtained by adding 0.1 N (0.1 mol/L) sodium hydroxide (manufactured by Wako Pure Chemical Industries, Ltd.) to the obtained mixed solution little by little, adjusting the pH value to 7.8, and adding injection water thereto such that the total amount of the mixed solution became 2.5 g.

The obtained aqueous composition was placed in a glove box, and substitution of gas in the aqueous composition with nitrogen was performed (concentration of dissolved oxygen:

0.01 ppm) by stirring the aqueous composition for 2 hours at room temperature under nitrogen atmosphere. Thereafter, the aqueous composition was sterilized and filtered using a 0.2 μm filter (made of PTFE) under nitrogen atmosphere (oxygen concentration: 1.0 volume %, temperature: 25.0° C.). Then, a vial (manufactured by Fuji Glass Co., Ltd., VIAL BOTTLE 3010 SILICORT) was filled with 2 mL of the sterilized and filtered aqueous composition. The volume of gas within this container (vial) when being filled with the aqueous composition was 2.3 mL.

A target injection preparation (C-1, the content of pemetrexed in the aqueous composition: 2.50 mass %, the content of cysteine hydrochloride in the aqueous composition: 0.051 mass %, and the content of thioglycerol in the aqueous composition: 0.076 mass %) was obtained by tightly plugging the vial with a rubber plug (manufactured by Daikyo Seiko. Ltd.) which had been subjected to laminate coating, putting an aluminum seal (manufactured by Nichiden-Rika Glass Co., Ltd., ALUMINUM SEAL B (middle)) so as to cover the vial and the mouth of the rubber plug, and clamping the aluminum seal, with which the vial and the mouth of the rubber plug are put, from the above using a clipper.

Example 2: Preparation of Injection Preparation (C-2)

A target injection preparation (C-2, the content of pemetrexed in the aqueous composition: 2.50 mass %, the content of cysteine hydrochloride in the aqueous composition: 0.024 mass %, and the content of thioglycerol in the aqueous composition: 0.036 mass %) was obtained similarly to Example 1 except that the amount of cysteine hydrochloride in Example 1 was changed from 128.0 mg to 60.0 mg and the amount of thioglycerol was changed from 190.0 mg to 90.0 mg.

Example 3: Preparation of Injection Preparation (C-3)

A target injection preparation (C-3, the content of pemetrexed in the aqueous composition: 2.50 mass %, the content of cysteine hydrochloride in the aqueous composition: 0.051 mass %, and the content of thioglycerol in the aqueous composition: 0.076 mass %) was obtained similarly to Example 1 except that the pH of the aqueous composition in Example 1 was changed from 7.8 to 8.5.

Example 4: Preparation of Injection Preparation (C-4)

A target injection preparation (C-4, the content of pemetrexed in the aqueous composition: 2.50 mass %, the content of cysteine hydrochloride in the aqueous composition: 0.051 mass %, and the content of thioglycerol in the aqueous composition: 0.076 mass %) was obtained similarly to Example 1 except that the pH of the aqueous composition in Example 1 was changed from 7.8 to 6.5.

Example 5: Preparation of Injection Preparation (C-5)

A target injection preparation (C-5, the content of pemetrexed in the aqueous composition: 2.50 mass %, the content of cysteine hydrochloride in the aqueous composition: 0.051 mass %, and the content of thioglycerol in the aqueous composition: 0.057 mass %) was obtained similarly to Example 1 except that the amount of thioglycerol in Example 1 was changed from 190.0 mg to 143.0 mg.

Example 6: Preparation of Injection Preparation (C-6)

A target injection preparation (C-6, the content of pemetrexed in the aqueous composition: 2.50 mass %, the content of cysteine hydrochloride in the aqueous composition: 0.051 mass %, and the content of thioglycerol in the aqueous composition: 0.036 mass %) was obtained similarly to Example 1 except that the amount of thioglycerol in Example 1 was changed from 190.0 mg to 90.0 mg.

Example 7: Preparation of Injection Preparation (C-7)

A target injection preparation (C-7, the content of pemetrexed in the aqueous composition: 2.50 mass %, the content of cysteine hydrochloride in the aqueous composition: 0.051 mass %, and the content of thioglycerol in the aqueous composition: 0.019 mass %) was obtained similarly to Example 1 except that the amount of thioglycerol in Example 1 was changed from 190.0 mg to 48.0 mg.

Example 8: Preparation of Injection Preparation (C-8)

A target injection preparation (C-8, the content of pemetrexed in the aqueous composition: 2.50 mass %, the content of cysteine hydrochloride in the aqueous composition: 0.036 mass %, and the content of thioglycerol in the aqueous composition: 0.076 mass %) was obtained similarly to Example 1 except that the amount of cysteine hydrochloride in Example 1 was changed from 128.0 mg to 90.0 mg.

Example 9: Preparation of Injection Preparation (C-9)

A target injection preparation (C-9, the content of pemetrexed in the aqueous composition: 2.50 mass %, the content of cysteine hydrochloride in the aqueous composition: 0.024 mass %, and the content of thioglycerol in the aqueous composition: 0.076 mass %) was obtained similarly to Example 1 except that the amount of cysteine hydrochloride in Example 1 was changed from 128.0 mg to 60.0 mg.

Example 10: Preparation of Injection Preparation (C-10)

A target injection preparation (C-10, the content of pemetrexed in the aqueous composition: 2.50 mass %, the content of cysteine hydrochloride in the aqueous composition: 0.013 mass %, and the content of thioglycerol in the aqueous composition: 0.076 mass %) was obtained similarly to Example 1 except that the amount of cysteine hydrochloride in Example 1 was changed from 128.0 mg to 33.0 mg.

Example 11: Preparation of Injection Preparation (C-11)

A target injection preparation (C-11, the content of pemetrexed in the aqueous composition: 2.50 mass %, the content of cysteine hydrochloride in the aqueous composition: 0.051 mass %, and the content of thioglycerol in the aqueous composition: 0.076 mass %) was obtained similarly to Example 1 except that the conditions of sterilizing and filtering the aqueous composition in Example 1 was changed from the nitrogen atmosphere at an oxygen concentration of 1.0 volume % and a temperature of 25.0° C. to nitrogen atmosphere at an oxygen concentration of 1.2 volume % and a temperature of 25.0° C.

Example 12: Preparation of Injection Preparation (C-12)

A target injection preparation (C-12, the content of pemetrexed in the aqueous composition: 2.50 mass %, the content of cysteine hydrochloride in the aqueous composition: 0.051 mass %, and the content of thioglycerol in the aqueous composition: 0.076 mass %) was obtained similarly to Example 1 except that the conditions of sterilizing and filtering the aqueous composition in Example 1 was changed from the nitrogen atmosphere at an oxygen concentration of 1.0 volume % and a temperature of 25.0° C. to nitrogen atmosphere at an oxygen concentration of 2.0 volume % and a temperature of 25.0° C.

Comparative Example 1: Preparation of Injection Preparation (R-1)

A target injection preparation (R-1, the content of pemetrexed in the aqueous composition: 2.50 mass % and the content of cysteine hydrochloride in the aqueous composition: 0.051 mass %) was obtained similarly to Example 1 except that the constitution of the aqueous composition in Example 1 was changed from 2.00 g of injection water, pemetrexed disodium (62.5 mg as pemetrexed), 128.0 mg of a 1 mass % aqueous solution of cysteine hydrochloride, and 190.0 mg of a 1 mass % aqueous solution of thioglycerol to 2.00 g of injection water, pemetrexed disodium (62.5 mg as pemetrexed), and 128.0 mg of a 1 mass % aqueous solution of cysteine hydrochloride.

Comparative Example 2: Preparation of Injection Preparation (R-2)

A target injection preparation (R-2, the content of pemetrexed in the aqueous composition: 2.50 mass % and the content of thioglycerol in the aqueous composition: 0.076 mass %) was obtained similarly to Example 1 except that the constitution of the aqueous composition in Example 1 was changed from 2.00 g of injection water, pemetrexed disodium (62.5 mg as pemetrexed), 128.0 mg of a 1 mass % aqueous solution of cysteine hydrochloride, and 190.0 mg of a 1 mass % aqueous solution of thioglycerol to 2.00 g of injection water, pemetrexed disodium (62.5 mg as pemetrexed), and 190.0 mg of a 1 mass % aqueous solution of thioglycerol.

Comparative Example 3: Preparation of Injection Preparation (R-3)

A target injection preparation (R-3, the content of pemetrexed in the aqueous composition: 2.50 mass %, the content of cysteine hydrochloride in the aqueous composition: 0.051 mass %, and the content of sodium thioglycolate in the aqueous composition: 0.062 mass %) was obtained similarly to Example 1 except that the constitution of the aqueous composition in Example 1 was changed from 2.00 g of injection water, pemetrexed disodium (62.5 mg as pemetrexed), 128.0 mg of a 1 mass % aqueous solution of cysteine hydrochloride, and 190.0 mg of a 1 mass % aqueous solution of thioglycerol to 2.00 g of injection water, pemetrexed disodium (62.5 mg as pemetrexed), 128.0 mg of a 1 mass % aqueous solution of cysteine hydrochloride, and 155.0 mg of a 1 mass % aqueous solution of sodium thioglycolate (manufactured by Wako Pure Chemical Industries, Ltd.) which had been prepared in advance.

Comparative Example 4: Preparation of Injection Preparation (R-4)

A target injection preparation (R-4, the content of pemetrexed in the aqueous composition: 2.50 mass %, the content of thioglycerol in the aqueous composition: 0.076 mass %, and the content of sodium thioglycolate in the aqueous composition: 0.062 mass %) was obtained similarly to Example 1 except that the constitution of the aqueous composition in Example 1 was changed from 2.00 g of injection water, pemetrexed disodium (62.5 mg as pemetrexed), 128.0 mg of a 1 mass % aqueous solution of cysteine hydrochloride, and 190.0 mg of a 1 mass % aqueous solution of thioglycerol to 2.00 g of injection water, pemetrexed disodium (62.5 mg as pemetrexed), 190.0 mg of a 1 mass % aqueous solution of thioglycerol, and 155.0 mg of a 1 mass % aqueous solution of sodium thioglycolate (manufactured by Wako Pure Chemical Industries, Ltd.).

Comparative Example 5: Preparation of Injection Preparation (R-5)

2.00 g of injection water (manufactured by Hikari Pharmaceutical Co., Ltd.), pemetrexed disodium (100.0 mg as pemetrexed), and 75.0 mg of a 1 mass % aqueous solution of cysteine hydrochloride (manufactured by KYOWA HAKKO BIO CO. LTD., L-cysteine hydrochloride monohydrate) which had been prepared in advance were weighed into a clean 10 mL vial in which a stirrer was placed, and were stirred and dissolved for 10 minutes at room temperature. Determination as to whether or not the mixed solution became a homogeneous and clear solution was performed through visual observation. Specifically, it was determined that the dissolution was completed when dissolution residues were not recognized while externally observing the mixed solution with the naked eye.

An aqueous composition was obtained by adding 0.1 N (0.1 mol/L) sodium hydroxide (manufactured by Wako Pure Chemical Industries, Ltd.) to the obtained mixed solution little by little, adjusting the pH value to 8.5, and adding injection water thereto such that the total amount of the mixed solution became 2.50 g.

The obtained aqueous composition was placed in a glove box, and substitution of gas in the aqueous composition with nitrogen was performed (concentration of dissolved oxygen: 0.01 ppm) by stirring the aqueous composition for 2 hours at room temperature under nitrogen atmosphere. Thereafter, the aqueous composition was sterilized and filtered using a 0.2 μm filter (made of PTFE) under nitrogen atmosphere (oxygen concentration: 5.0 volume %, temperature: 25.0° C.). Then, a vial (manufactured by Fuji Glass Co., Ltd., VIAL BOTTLE 3010 SILICORT) was filled with 2 mL of the sterilized and filtered aqueous composition. The volume of gas within this container (vial) when being filled with the aqueous composition was 2.3 mL.

A target injection preparation (R-5, the content of pemetrexed in the aqueous composition: 4.00 mass % and the content of cysteine hydrochloride in the aqueous composition: 0.030 mass %) was obtained by tightly plugging the vial with a rubber plug (manufactured by Daikyo Seiko. Ltd.) which had been subjected to laminate coating, putting an aluminum seal (manufactured by Nichiden-Rika Glass Co., Ltd., ALUMINUM SEAL B (middle)) so as to cover the vial and the mouth of the rubber plug, and clamping the aluminum seal, with which the vial and the mouth of the rubber plug are put, from the above using a clipper.

Comparative Example 6: Preparation of Injection Preparation (R-6)

2.00 g of injection water (manufactured by Hikari Pharmaceutical Co., Ltd.), pemetrexed disodium (100.0 mg as pemetrexed), and 75.0 mg of a 1 mass % aqueous solution of sodium thioglycolate (manufactured by Wako Pure Chemical Industries, Ltd.) which had been prepared in advance were weighed into a clean 10 mL vial in which a stirrer was placed, and were stirred and dissolved for 10 minutes at room temperature. Determination as to whether or not the mixed solution became a homogeneous and clear solution was performed through visual observation. Specifically, it was determined that the dissolution was completed when dissolution residues were not recognized while externally observing the mixed solution with the naked eye.

An aqueous composition was obtained by adding 0.1 N (0.1 mol/L) sodium hydroxide (manufactured by Wako Pure Chemical Industries, Ltd.) to the obtained mixed solution little by little, adjusting the pH value to 8.5, and adding injection water thereto such that the total amount of the mixed solution became 2.50 g.

The obtained aqueous composition was placed in a glove box, and substitution of gas in the aqueous composition with nitrogen was performed (concentration of dissolved oxygen: 0.01 ppm) by stirring the aqueous composition for 2 hours at room temperature under nitrogen atmosphere. Thereafter, the aqueous composition was sterilized and filtered using a 0.2 μm filter (made of PTFE) under nitrogen atmosphere (oxygen concentration: 5.0 volume %, temperature: 25.0° C.). Then, a vial (manufactured by Fuji Glass Co., Ltd., VIAL BOTTLE 3010 SILICORT) was filled with 2 mL of the sterilized and filtered aqueous composition. The volume of gas within this container (vial) when being filled with the aqueous composition was 4.3 mL.

A target injection preparation (R-6, the content of pemetrexed in the aqueous composition: 4.00 mass % and the content of sodium thioglycolate in the aqueous composition: 0.030 mass %) was obtained by tightly plugging the vial with a rubber plug (manufactured by Daikyo Seiko. Ltd.) which had been subjected to laminate coating, putting an aluminum seal (manufactured by Nichiden-Rika Glass Co., Ltd., ALUMINUM SEAL B (middle)) so as to cover the vial and the mouth of the rubber plug, and clamping the aluminum seal, with which the vial and the mouth of the rubber plug are put, from the above using a clipper.

Comparative Example 7: Preparation of Injection Preparation (C-7)

A target injection preparation (R-7, the content of pemetrexed in the aqueous composition: 2.50 mass %, the content of cysteine hydrochloride in the aqueous composition: 0.051 mass %, and the content of thioglycerol in the aqueous composition: 0.076 mass %) was obtained similarly to Example 1 except that the conditions of sterilizing and filtering the aqueous composition in Example 1 was changed from the nitrogen atmosphere at an oxygen concentration of 1.0 volume % and a temperature of 25.0° C. to nitrogen atmosphere at an oxygen concentration of 5.0 volume % and a temperature of 25.0° C.

The compositions of the injection preparations (C-1) to (C-12) and (R-1) to (R-7) are shown in Table 2. The symbol "-" in a column of formulation in Table 2 represents an unblended state. In addition, in Table 2, the "ratio of the content of cysteine hydrochloride to the content of pemetrexed in an aqueous composition (the content of pemetrexed: the content of cysteine hydrochloride)" is denoted as a "mass ratio of cysteine hydrochloride to pemetrexed", the "ratio of the content of thioglycerol to the content of pemetrexed in an aqueous composition (the content of pemetrexed: the content of thioglycerol)" is denoted as a "mass ratio of thioglycerol to pemetrexed", and the "ratio of the content of thioglycerol to the content of cysteine hydrochloride in an aqueous composition (the content of cysteine hydrochloride: the content of thioglycerol)" is denoted as a "mass ratio of thioglycerol to cysteine hydrochloride".

[Measurement of Concentration of Dissolved Oxygen in Aqueous Composition]

The concentration of dissolved oxygen in an aqueous composition contained in each injection preparation was measured using the following determination device and through the following measurement method.

Determination device: InLab (registered trademark) Science Pro ISM (manufactured by Mettler-Toledo International Inc.)

Measurement method: The concentration of dissolved oxygen in an aqueous composition contained in each injection preparation was measured by bringing an electrode of the oxygen concentration determination device into contact with the aqueous composition under nitrogen atmosphere (concentration of oxygen in gas: less than 0.1 volume %) in the glove box

[Measurement of Concentration of Oxygen in Gas within Container]

The concentration of oxygen in gas within a container of each injection preparation was measured using the following determination device and through the following measurement method. The measurement values are shown in Table 2.

Determination device: residual oxygen meter (product name: PACK MASTER, manufactured by Iijima Electronics Corporation)

Measurement method: diaphragm-type galvanic cell type

Specifically, the concentration of oxygen in gas within a container of each injection preparation was measured by sticking a sampler needle portion of an oxygen concentration determination device into the container of each injection preparation and suctioning gas in a head space within the container in each injection preparation under nitrogen atmosphere (concentration of oxygen in gas: less than 0.1 volume %) in a glove box.

[Ratio of Number of Oxygen Molecules with Respect to Number of Pemetrexed Molecules in Injection Preparation]

The ratio (number of oxygen molecules/number of pemetrexed molecules) of the number of oxygen molecules with respect to the number of pemetrexed molecules in the injection preparation was calculated through the following method. The calculated values are shown in Table 2.

Number (mol) of pemetrexed molecules in injection preparation=concentration (mol/L) of pemetrexed in aqueous composition×volume (L) of aqueous composition   Equation 1.

Number (mol) of oxygen molecules in injection preparation=number (mol) of oxygen molecules in gas within container+number (mol) of oxygen molecules in aqueous composition   Equation 2.

Number (mol) of oxygen molecules in gas within container=concentration (volume %) of oxygen in gas within container÷100×volume (L) of gas within container÷(0.082×(273.15+temperature (° C.)))   Equation 3.

Number (mol) of oxygen molecules in aqueous composition=concentration (mg/L) of dissolved oxygen in aqueous composition÷32÷1000×volume (L) of aqueous composition   Equation 4.

[Evaluation]

Regarding the obtained injection preparations (C-1) to (C-12) and (R-1) to (R-7), stress testing was performed in which each injection preparation which was placed in LAMIZIP (made of PET (polyethylene terephthalate)/AL) with AGELESS (Z-100 PKC, manufactured by Mitsubishi Gas Chemical Company, Inc.) and was subjected to heat sealing under nitrogen atmosphere (oxygen concentration in gas: 0.5 volume % to 0.7 volume %) was preserved in a constant-temperature tank at 70° C. for 1 week.

Thereafter, an evaluation of preservation stability of each injection preparation which has been determined from decomposition of pemetrexed and coloration of an aqueous composition were performed through the method described below. The evaluation results are shown in Table 2.

1. Preservation Stability (Evaluation Determined from Decomposition of Pemetrexed)

A sample liquid after stress testing was obtained after weighing about 10 mg of an aqueous composition after the stress testing into a 1 mL volumetric flask, and diluting the aqueous composition with ultrapure water. A sample liquid before the stress testing was also obtained by preparing an aqueous composition before the stress testing through the same method.

Quantitative determination of decomposition products of pemetrexed was performed using a high performance liquid chromatograph. In the following measurement condition, the amount of decomposition products (hereinafter, referred to as an "analog A") which have been detected at a holding time of 16.6 minutes and the amount of decomposition products (hereinafter, referred to as an "analog B") which have been detected at a holding time of 23.2 minutes as a unimodal peak are quantitatively determined as decomposition products of pemetrexed. The composition of a development solvent is shown in Table 1.

(HPLC Measurement Condition)

Detector: UV detector (detection wavelength: 230 nm)

Column: CapcellPak C-18, UG120, 4.6×150 mm, manufactured by Shiseido Japan Co., Ltd.

Column temperature: 25° C.

Development solvent: A; 0.1 vol % phosphoric acid aqueous solution

B; Acetonitrile

Flow velocity: 1.5 mL/min

Temperature of sample cooler: 4° C.

Amount of injection: 5 μL

TABLE 1

| Development solvent composition: | |
|---|---|
| Time (minutes) | B Composition (%) |
| 0.01 | 10 |
| 25.00 | 16.25 |
| 25.01 | 70 |
| 35.00 | 70 |

TABLE 1-continued

| Development solvent composition: | |
|---|---|
| Time (minutes) | B Composition (%) |
| 35.01 | 10 |
| 45 | End |

Evaluation of preservation stability was performed by having the amounts of analog A and analog B generated through oxidation of pemetrexed as an indicator. The ratio (%) of the amount of analog A and analog B in the sample liquid after the stress testing to the amount of pemetrexed in the sample liquid before the stress testing was obtained based on each peak surface area, and evaluation of preservation stability which had been determined from decomposition of pemetrexed was performed in accordance with the following evaluation standard.

(Evaluation Standard)

A: less than 0.090%

B: greater than or equal to 0.090% and less than 0.180%

C: greater than or equal to 0.180%

2. Preservation Stability (Evaluation Determined from Coloration of Aqueous Composition)

The coloration of an aqueous composition after stress testing was quantitatively evaluated using a UV-visible spectrophotometer (manufactured by JASCO Corporation, V-630). Specifically, the absorbance at a wavelength of 420 nm was obtained by preparing a sample liquid which was obtained by diluting the aqueous composition after the stress testing with ultrapure water by 10 times. Then, evaluation of preservation stability determined from the coloration of the aqueous composition was performed in accordance with the following evaluation standard.

(Evaluation Standard)

A: less than 0.010

B: greater than or equal to 0.010 and less than 0.030

C: greater than or equal to 0.030

3. Comprehensive Evaluation

Comprehensive evaluation was performed in accordance with the following evaluation standard.

(Evaluation Standard)

A: Both of the evaluation determined from decomposition and the evaluation determined from coloration are A.

B: Both of the evaluation determined from decomposition and the evaluation determined from coloration are B, or any one of the evaluation determined from decomposition and the evaluation determined from coloration is A and the other is B.

C: Both of the evaluation determined from decomposition and the evaluation determined from coloration are C, or any one of the evaluation determined from decomposition and the evaluation determined from coloration is A or B, and the other is C.

TABLE 2

| | Composition and physical properties | | | | | | | |
|---|---|---|---|---|---|---|---|---|
| | (i) Pemetrexed (mass %) | (ii) Cysteine hydrochloride (mass %) | (iii) thioglycerol (mass %) | Sodium thioglycolate (mass %) | Mass ratio of cysteine hydrochloride to pemetrexed | Mass ratio of thioglycerol to pemetrexed | Mass ratio of thioglycerol to cysteine hydrochloride | Concentration (volume %) of oxygen in gas within container |
| Example 1 | 2.50 | 0.051 | 0.076 | — | 1:0.020 | 1:0.030 | 1:1.5 | 1.0 |
| Example 2 | 2.50 | 0.024 | 0.036 | — | 1:0.010 | 1:0.014 | 1:1.5 | 1.0 |
| Example 3 | 2.50 | 0.051 | 0.076 | — | 1:0.020 | 1:0.030 | 1:1.5 | 1.0 |
| Example 4 | 2.50 | 0.051 | 0.076 | — | 1:0.020 | 1:0.030 | 1:1.5 | 1.0 |
| Example 5 | 2.50 | 0.051 | 0.057 | — | 1:0.020 | 1:0.023 | 1:1.1 | 1.0 |
| Example 6 | 2.50 | 0.051 | 0.036 | — | 1:0.020 | 1:0.014 | 1:0.7 | 1.0 |
| Example 7 | 2.50 | 0.051 | 0.019 | — | 1:0.020 | 1:0.007 | 1:0.4 | 1.0 |
| Example 8 | 2.50 | 0.036 | 0.076 | — | 1:0.014 | 1:0.030 | 1:2.1 | 1.0 |
| Example 9 | 2.50 | 0.024 | 0.076 | — | 1:0.010 | 1:0.030 | 1:3.2 | 1.0 |
| Example 10 | 2.50 | 0.013 | 0.076 | — | 1:0.005 | 1:0.030 | 1:6.3 | 1.0 |
| Example 11 | 2.50 | 0.051 | 0.076 | — | 1:0.020 | 1:0.030 | 1:1.5 | 1.2 |

TABLE 2-continued

| | | | | | | | | |
|---|---|---|---|---|---|---|---|---|
| Example 12 | 2.50 | 0.051 | 0.076 | — | 1:0.020 | 1:0.030 | 1:1.5 | 2.0 |
| Comparative Example 1 | 2.50 | 0.051 | — | — | 1:0.020 | — | — | 1.0 |
| Comparative Example 2 | 2.50 | — | 0.076 | — | — | 1:0.030 | — | 1.0 |
| Comparative Example 3 | 2.50 | 0.051 | — | 0.062 | 1:0.020 | — | — | 1.0 |
| Comparative Example 4 | 2.50 | — | 0.076 | 0.062 | — | 1:0.030 | — | 1.0 |
| Comparative Example 5 | 4.00 | 0.030 | — | — | 1:0.012 | — | — | 5.0 |
| Comparative Example 6 | 4.00 | — | — | 0.030 | — | — | — | 5.0 |
| Comparative Example 7 | 2.50 | 0.051 | 0.076 | — | 1:0.020 | 1:0.030 | 1:1.5 | 5.0 |

| | Composition and physical properties | | Results (70° C., 1 week) | | | | | |
|---|---|---|---|---|---|---|---|---|
| | Ratio of number of oxygen molecules to number of pemetrexed molecules | pH | Decomposition | | | | Coloration | Comprehensive evaluation |
| | | | Amount of analog A (%) | | Amount of analog B (%) | | | |
| Example 1 | 0.0080 | 7.8 | 0.061 | A | 0.000 | A | 0.004 A | A |
| Example 2 | 0.0080 | 7.8 | 0.096 | B | 0.000 | A | 0.021 B | B |
| Example 3 | 0.0080 | 8.5 | 0.034 | A | 0.000 | A | 0.006 A | A |
| Example 4 | 0.0080 | 6.5 | 0.098 | B | 0.000 | A | 0.004 A | B |
| Example 5 | 0.0080 | 7.8 | 0.048 | A | 0.000 | A | 0.004 A | A |
| Example 6 | 0.0080 | 7.8 | 0.057 | A | 0.000 | A | 0.005 A | A |
| Example 7 | 0.0080 | 7.8 | 0.060 | A | 0.000 | A | 0.007 A | A |
| Example 8 | 0.0080 | 7.8 | 0.055 | A | 0.000 | A | 0.009 A | A |
| Example 9 | 0.0080 | 7.8 | 0.061 | A | 0.000 | A | 0.004 A | A |
| Example 10 | 0.0080 | 7.8 | 0.064 | A | 0.000 | A | 0.006 A | A |
| Example 11 | 0.0096 | 7.8 | 0.056 | A | 0.000 | A | 0.006 A | A |
| Example 12 | 0.0160 | 7.8 | 0.093 | B | 0.000 | A | 0.009 A | B |
| Comparative Example 1 | 0.0080 | 7.8 | 0.095 | B | 0.000 | A | 0.083 C | C |
| Comparative Example 2 | 0.0080 | 7.8 | 0.182 | C | 0.000 | A | 0.007 A | C |
| Comparative Example 3 | 0.0080 | 7.8 | 0.041 | A | 0.781 | C | 0.008 A | C |
| Comparative Example 4 | 0.0080 | 7.8 | 0.048 | A | 0.509 | C | 0.004 A | C |
| Comparative Example 5 | 0.0400 | 8.5 | 3.253 | C | 0.000 | A | 0.068 C | C |
| Comparative Example 6 | 0.0400 | 8.5 | 0.997 | C | 1.885 | C | 0.129 C | C |
| Comparative Example 7 | 0.0400 | 7.8 | 0.480 | C | 0.000 | A | 0.030 B | C |

From the results of Table 2, it became clear that it was possible to obtain an injection preparation in which decomposition of pemetrexed and coloration of an aqueous composition during preservation were suppressed (refer to Examples 1 to 12) by making the aqueous composition contain a specific amount of cysteine hydrochloride and a specific amount of thioglycerol in combination and making the concentration of oxygen in gas within a container be less than or equal to 2.0 volume %.

In addition, it became clear that it was possible to obtain an injection preparation in which decomposition of pemetrexed and coloration of an aqueous composition during preservation were suppressed (refer to Examples 1 to 12) by making the aqueous composition contain a specific amount of cysteine hydrochloride and a specific amount of thioglycerol in combination and making the ratio of the number of oxygen molecules to the number of pemetrexed molecules in the injection preparation be less than or equal to 0.0160.

In contrast, it became clear that it was impossible to suppress both or any one of the decomposition of pemetrexed and the coloration of an aqueous composition during preservation (refer to Comparative Examples 1 to 6) even if the aqueous composition was made to contain only any one of a specific amount of cysteine hydrochloride and a specific amount of thioglycerol.

In addition, it became clear that generation of the analog B was hardly suppressed (refer to Comparative Examples 3, 4, and 6) by making the aqueous composition contain cysteine hydrochloride or thioglycerol and sodium thioglycolate in combination.

It became clear that, even if an aqueous composition was made to contain a specific amount of cysteine hydrochloride and a specific amount of thioglycerol in combination, when the concentration of oxygen in gas within a container exceeded 2.0 volume %, an effect of suppressing decomposition of pemetrexed and an effect of suppressing coloration of an aqueous composition during preservation were both reduced (refer to Comparative Example 7).

In addition, it became clear that, even if an aqueous composition was made to contain a specific amount of cysteine hydrochloride and a specific amount of thioglycerol in combination, when the ratio of the number of oxygen molecules to the number of pemetrexed molecules in the injection preparation exceeded 0.0160, an effect of suppressing decomposition of pemetrexed and an effect of suppressing coloration of an aqueous composition during preservation were both reduced (refer to Comparative Example 7).

The entire disclosure of JP2014-069613, filed Mar. 28, 2014 is incorporated in the present specification for reference.

All of the documents, patent applications, and technical standards described in the present specification are incorporated in the present specification for reference to the same extent as a case where incorporation of individual document, patent application, and technical standard for reference is specifically and individually stated.

What is claimed is:

1. An injection preparation comprising:
   an aqueous composition containing the following (i), (ii), (iii), and (iv); and
   a container which seals the aqueous composition,
   wherein a concentration of oxygen in gas within the container which seals the aqueous composition is less than or equal to 1.5 volume %:
   (i) pemetrexed or a salt thereof;
   (ii) at least one antioxidant agent A which is selected from the group consisting of cysteine and a salt thereof, and of which the content is 0.001 mass % to 0.1 mass % with respect to the total mass of the aqueous composition;
   (iii) thioglycerol of which the content is 0.001 mass % to 0.1 mass % with respect to the total mass of the aqueous composition, wherein a ratio of the content of thioglycerol to the content of pemetrexed or a salt thereof in the aqueous composition is 1:0.007 to 1:0.031 on a mass basis; and
   (iv) an aqueous solvent of which the content is greater than or equal to 50 mass % with respect to the total mass of the aqueous composition,
   wherein a ratio of the content of thioglycerol to the content of the antioxidant agent A in the aqueous composition is 1:0.3 to 1:6.5 on a mass basis, and
   wherein the pH of the aqueous composition is 7.0 to 9.0.

2. The injection preparation according to claim 1, wherein a ratio of the content of the antioxidant agent A to the content of pemetrexed or a salt thereof in the aqueous composition is 1:0.005 to 1:0.020 on a mass basis.

3. The injection preparation according to claim 1, wherein at least one of a ratio of the content of the antioxidant agent A with respect to the content of pemetrexed or a salt thereof in the aqueous composition being greater than or equal to 0.011 on a mass basis, or a ratio of the content of thioglycerol with respect to the content of pemetrexed or a salt thereof in the aqueous composition being greater than or equal to 0.015 on a mass basis is satisfied.

4. The injection preparation according to claim 1, wherein a ratio of the content of thioglycerol to the content of pemetrexed or a salt thereof in the aqueous composition is 1:0.015 to 1:0.031 on a mass basis.

5. An injection preparation comprising:
   an aqueous composition containing the following (i), (ii), (iii), and (iv); and
   a container which seals the aqueous composition,
   wherein a ratio of the number of oxygen molecules with respect to the number of pemetrexed molecules in the injection preparation is less than or equal to 0.0096:
   (i) pemetrexed or a salt thereof;
   (ii) at least one antioxidant agent A which is selected from the group consisting of cysteine and a salt thereof, and of which the content is 0.001 mass % to 0.1 mass % with respect to the total mass of the aqueous composition;
   (iii) thioglycerol of which the content is 0.001 mass % to 0.1 mass % with respect to the total mass of the aqueous composition, wherein a ratio of the content of thioglycerol to the content of pemetrexed or a salt thereof in the aqueous composition is 1:0.007 to 1:0.031 on a mass basis; and
   (iv) an aqueous solvent of which the content is greater than or equal to 50 mass % with respect to the total mass of the aqueous composition,
   wherein a ratio of the content of thioglycerol to the content of the antioxidant agent A in the aqueous composition is 1:0.3 to 1:6.5 on a mass basis, and
   wherein the pH of the aqueous composition is 7.0 to 9.0.

6. The injection preparation according to claim 5, wherein a ratio of the content of the antioxidant agent A to the content of pemetrexed or a salt thereof in the aqueous composition is 1:0.005 to 1:0.020 on a mass basis.

7. The injection preparation according to claim 5, wherein at least one of a ratio of the content of the antioxidant agent A with respect to the content of pemetrexed or a salt thereof in the aqueous composition being greater than or equal to 0.011 on a mass basis, or a ratio of the content of thioglycerol with respect to the content of pemetrexed or a salt thereof in the aqueous composition being greater than or equal to 0.015 on a mass basis is satisfied.

8. The injection preparation according to claim 5, wherein a ratio of the content of thioglycerol to the content of pemetrexed or a salt thereof in the aqueous composition is 1:0.015 to 1:0.031 on a mass basis.

9. A method for producing an injection preparation comprising:
   preparing an aqueous composition which contains (i) pemetrexed or a salt thereof, (ii) at least one antioxidant agent A which is selected from the group consisting of cysteine and a salt thereof, and of which the content is 0.001 mass % to 0.1 mass % with respect to the total mass of the aqueous composition, (iii) thioglycerol of which the content is 0.001 mass % to 0.1 mass % with respect to the total mass of the aqueous composition, and (iv) an aqueous solvent of which the content is greater than or equal to 50 mass % with respect to the total mass of the aqueous composition; and
   filling a container with the aqueous composition under an inert gas atmosphere or substituting gas within the container with inert gas after filling the container with the aqueous composition, wherein
   a ratio of the content of thioglycerol to the content of pemetrexed or a salt thereof in the aqueous composition is 1:0.007 to 1:0.031 on a mass basis, and
   a concentration of oxygen in gas within the container which seals the aqueous composition is less than or equal to 1.5 volume %,
   wherein a ratio of the content of thioglycerol to the content of the antioxidant agent A in the aqueous composition is 1:0.3 to 1:6.5 on a mass basis, and
   wherein the pH of the aqueous composition is 7.0 to 9.0.

10. The method for producing an injection preparation according to claim 9, wherein the inert gas is nitrogen.

11. The method for producing an injection preparation according to claim 9, wherein a ratio of the content of thioglycerol to the content of pemetrexed or a salt thereof in the aqueous composition is 1:0.015 to 1:0.031 on a mass basis.

* * * * *